US012629541B2

(12) United States Patent
Wang et al.

(10) Patent No.: US 12,629,541 B2
(45) Date of Patent: May 19, 2026

(54) UNLOCKING ASSEMBLY, HUMAN BODY FIXING APPARATUS AND UNLOCKING METHOD FOR THE UNLOCKING ASSEMBLY

(71) Applicant: KLARITY MEDICAL & EQUIPMENT(GZ) CO., LTD., Guangdong (CN)

(72) Inventors: Wei Wang, Guangdong (CN); Lintao Li, Guangdong (CN); Qing Zhao, Guangdong (CN); Peiqin Lan, Guangdong (CN)

(73) Assignee: KLARITY MEDICAL & EQUIPMENT(GZ) CO., LTD., Guangdong (CN)

( * ) Notice: Subject to any disclaimer, the term of this patent is extended or adjusted under 35 U.S.C. 154(b) by 794 days.

(21) Appl. No.: 18/282,543

(22) PCT Filed: Feb. 25, 2020

(86) PCT No.: PCT/CN2020/076586
§ 371 (c)(1),
(2) Date: Sep. 18, 2023

(87) PCT Pub. No.: WO2021/128568
PCT Pub. Date: Jul. 1, 2021

(65) Prior Publication Data
US 2024/0238615 A1     Jul. 18, 2024

(30) Foreign Application Priority Data
Dec. 24, 2019    (CN) .......................... 201911354178.5

(51) Int. Cl.
*A61N 5/10*       (2006.01)

(52) U.S. Cl.
CPC ........ *A61N 5/10* (2013.01); *A61N 2005/1096* (2013.01); *A61N 2005/1097* (2013.01)

(58) Field of Classification Search
CPC .............. A61N 5/10; A61N 2005/1096; A61N 2005/1097; A61N 2005/1092; A61F 5/37;
(Continued)

(56) References Cited

U.S. PATENT DOCUMENTS 3,466,863 A * 9/1969 Wachendorf ............. D01H 9/04
57/273

FOREIGN PATENT DOCUMENTS

| CN | 200963438 | 10/2007 |
| CN | 201543116 | 8/2010 |

(Continued)

OTHER PUBLICATIONS

Machine translation of Publication No. Cn 209751978U created Sep. 11, 2025 from espacenet.com (Year: 2019).*
(Continued)

*Primary Examiner* — Alireza Nia
*Assistant Examiner* — Gina Mccarthy
(74) *Attorney, Agent, or Firm* — JCIPRNET

(57) ABSTRACT

An unlocking assembly includes a fixing plate, locking bodies, and a flexible member. The fixing plate is provided with fixing holes; the locking bodies are movably mounted in the fixing holes; the flexible member is connected to the locking bodies and is configured to drive the locking bodies to move towards a direction extending out of the fixing holes.

13 Claims, 7 Drawing Sheets

(58) Field of Classification Search
CPC .......... A61F 5/3707; A61H 2201/1604; A61H
2201/1607; A61H 2205/02; A61G 7/07;
A61G 7/072; A61G 13/121
See application file for complete search history.

(56) References Cited

FOREIGN PATENT DOCUMENTS

| | | |
|---|---|---|
| CN | 209137789 | 7/2019 |
| CN | 209751978 | 12/2019 |
| CN | 209751978 U | * 12/2019 |

OTHER PUBLICATIONS

"International Search Report (Form PCT/ISA/210) of PCT/CN2020/076586", mailed on Jun. 23, 2020, with English translation thereof, pp. 1-4.

* cited by examiner

100

200

300

400

200

310

140

130

520    510

500

320    310

100

300

600

UNLOCKING ASSEMBLY, HUMAN BODY FIXING APPARATUS AND UNLOCKING METHOD FOR THE UNLOCKING ASSEMBLY

CROSS-REFERENCE TO RELATED APPLICATION

This application is a 371 of international application of PCT application serial no. PCT/CN2020/076586, filed on Feb. 25, 2020, which claims priority to Chinese Patent Application No. 201911354178.5, filed on Dec. 24, 2019. The entirety of each of the above-mentioned patent applications is hereby incorporated by reference herein and made a part of this specification.

TECHNICAL FIELD

The present disclosure relates to the technical field of medical devices, and in particular to, an unlocking assembly and a human body fixing apparatus.

BACKGROUND

Tumor radiation therapy is a local treatment method of using radiation to treat tumors. Radiation rays include α, β, and γ rays produced by radioactive isotopes, as well as various x-rays, electron beams, proton beams, and other particle beams generated by x-ray treatment machines or accelerators. Approximately 70% of cancer patients require radiation therapy during their cancer treatment, and about 40% of cancers can be cured through the radiotherapy.

During the radiation therapy, it is necessary to use a fixing apparatus to fix the human body between a low-temperature thermoplastic sheet and a baseplate. The low-temperature thermoplastic sheet and the specific baseplate being used for the fixing apparatus ensures that the patient remains in a fixed position during the overall radiotherapy. This is conducive to precisely killing the cancer cells in the tumor area by the radiation.

However, the fixing apparatuses available on the market, once locked, can be unlocked only after being approached. If an emergency occurs to the patient and the fixing apparatuses cannot be unlocked in time, the patient is trapped between the low-temperature thermoplastic sheet and the fixing bottom plate, thus being unmovable. Because the doctor is generally outside the treatment room, they need to rush inside upon discovering the problem and to approach the fixing apparatuses to unlock the plurality of fixing apparatuses. This often leads to the miss of the best time to save the patient.

SUMMARY

An objective of the present disclosure is to provide an unlocking assembly and a human body fixing apparatus, to alleviate the technical problem in the related art that the fixing apparatus is unlocked only after being approached, requiring cumbersome unlocking steps and long time.

According to a first aspect, the present disclosure provides an unlocking assembly, including a fixing plate, a locking main body, and a flexible component.

The fixing plate is provided with a fixing hole, and the locking main body is movably mounted in the fixing hole.

The flexible component is connected to the locking main body, and the flexible component is configured to be able to drive the locking main body to move in a protruding direction from the fixing hole.

Optionally, the flexible component is disposed in the fixing plate and below the locking main body, and the flexible component is in an expanding state or a compressed state.

When the flexible component is in the expanding state, the locking main body protrudes out of the fixing hole.

When the flexible component is in the compressed state, the locking main body is inserted into the fixing hole.

Optionally, the unlocking assembly further includes an inflating and deflating component.

An end of the flexible component extends out of the fixing plate to be connected to the inflating and deflating component, and the inflating and deflating component is configured to be able to control the flexible component to switch between an expanding state and the compressed state.

Optionally, the flexible component includes an inflatable hose.

The fixing plate is provided with a guide groove, the inflatable hose is disposed in the guide groove, the locking main body is provided in plurality, and the plurality of locking main bodies are spaced apart along the inflatable hose.

Optionally, the flexible component further includes an air-bag protruding portion.

The air-bag protruding portion is disposed on the inflatable hose, and the air-bag protruding portion abuts against the locking main body.

Optionally, an end of the locking main body close to the flexible component is provided with an extending portion configured to increase an overall length.

Optionally, the extending portion includes a stud and a limit ring.

The stud is connected to the locking main body, the limit ring is connected to an end of the stud away from the locking main body, the limit ring includes an abut surface, and the abut surface abuts against the flexible component.

Optionally, the abut surface of the limit ring abuts against the air-bag protruding portion.

Optionally, the extending portion includes an abut surface, and the abut surface abuts against the air-bag protruding portion of the flexible component.

Optionally, an end of the inflatable hose away from the inflating and deflating component is provided with a sealing plug.

Optionally, the fixing plate includes a fixing bottom plate and a fixing cover plate.

The fixing cover plate covers the fixing bottom plate, and the flexible component is clamped between the fixing cover plate and the fixing bottom plate.

According to a second aspect, the present disclosure provides a human body fixing apparatus, including the unlocking assembly.

According to a third aspect, an unlocking method for the unlocking assembly according to the present disclosure is provided, including unlocking steps: 1) controlling the flexible component to drive the locking main body to move in a protruding direction from the fixing hole of the fixing plate, and 2) enabling the locking main body to protrude out of the fixing hole, to release locking of the locking main body.

Further, in step 1), the inflating and deflating component inflates the flexible component, such that the flexible component switches from a compressed state to an expanding state, and the flexible component drives the locking main body to move in a protruding direction from the fixing hole of the fixing plate.

Optionally, in step 1), the air-bag protruding portion of the flexible component pushes the abut surface of the limit ring, such that the flexible component drives the locking main body to move in the protruding direction from the fixing hole of the fixing plate, where the extending portion of the locking main body includes the stud and the limit ring.

The unlocking assembly provided by the present disclosure includes a fixing plate, a locking main body, and a flexible component. The fixing plate is provided with a fixing hole, and the locking main body is movably mounted in the fixing hole. The flexible component is connected to the locking main body, and the flexible component is configured to be able to drive the locking main body to move in a protruding direction from the fixing hole. The locking main body is retractably mounted in the fixing hole of the fixing plate, and the flexible component is able to drive the locking main body to move in the protruding direction from the fixing hole, so as to release the locking between the locking main body and the fixing hole. Therefore, the locking can be released by only controlling the flexible component at a long distance, alleviating the technical problem in the prior art that the fixing apparatus is unlocked only after being approached, requiring cumbersome unlocking steps and long time. In this way, during the radiation therapy, it is easy to unlock the fixing apparatus, consuming less time.

BRIEF DESCRIPTION OF DRAWINGS

To describe the technical solutions in the specific implementations of the present disclosure or in the related art more clearly, the following briefly describes the accompanying drawings required for describing the specific implementations or the related art. Apparently, the accompanying drawings in the following description show merely some of the implementations of the present disclosure, and persons of ordinary skill in the art may still derive other drawings from these accompanying drawings without creative efforts.

DETAILED DESCRIPTION OF EMBODIMENTS

Figure 1:
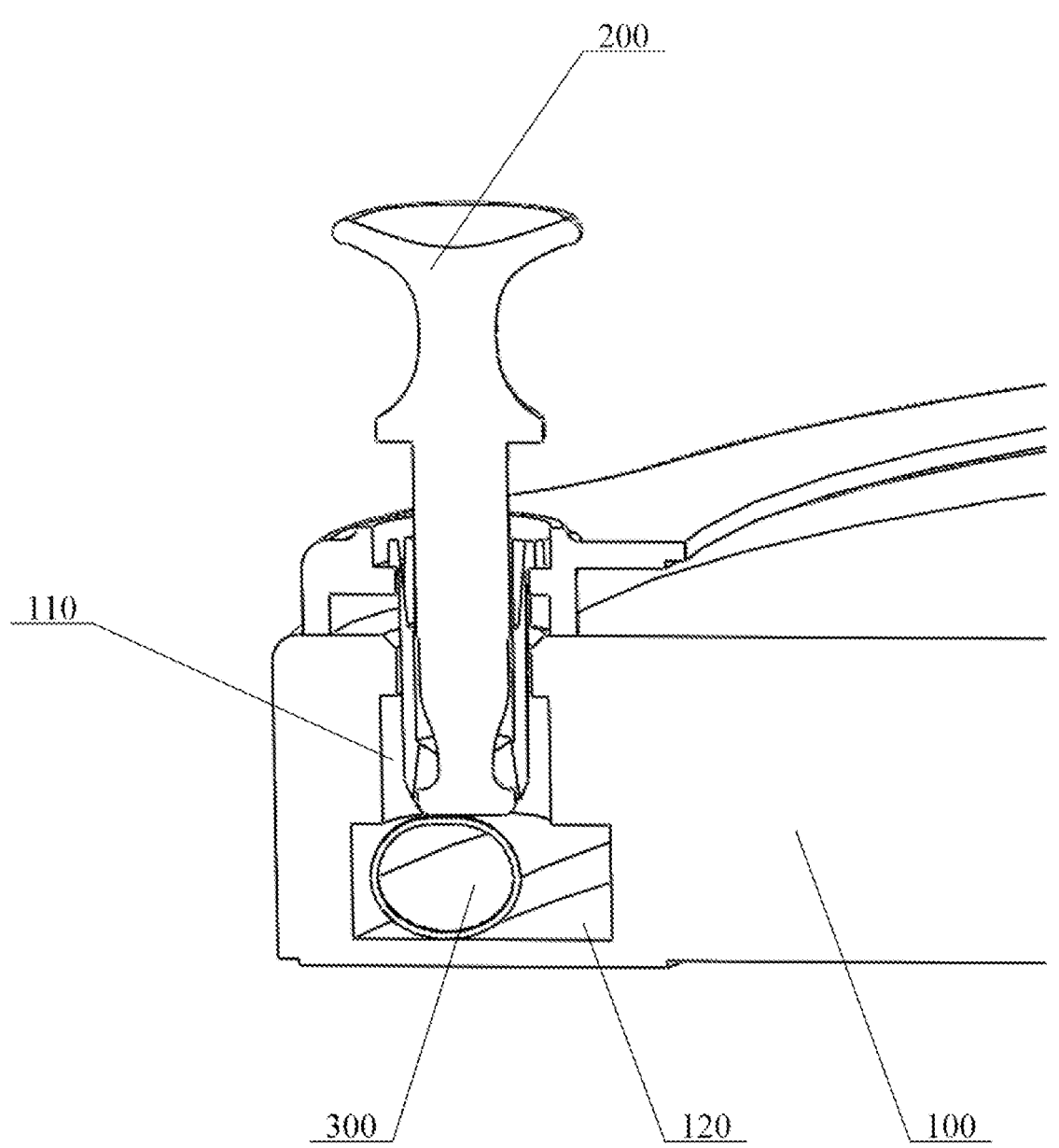
FIG. 1 is a cross section view of an unlocking assembly according to an embodiment of the present disclosure.
Figure 2:
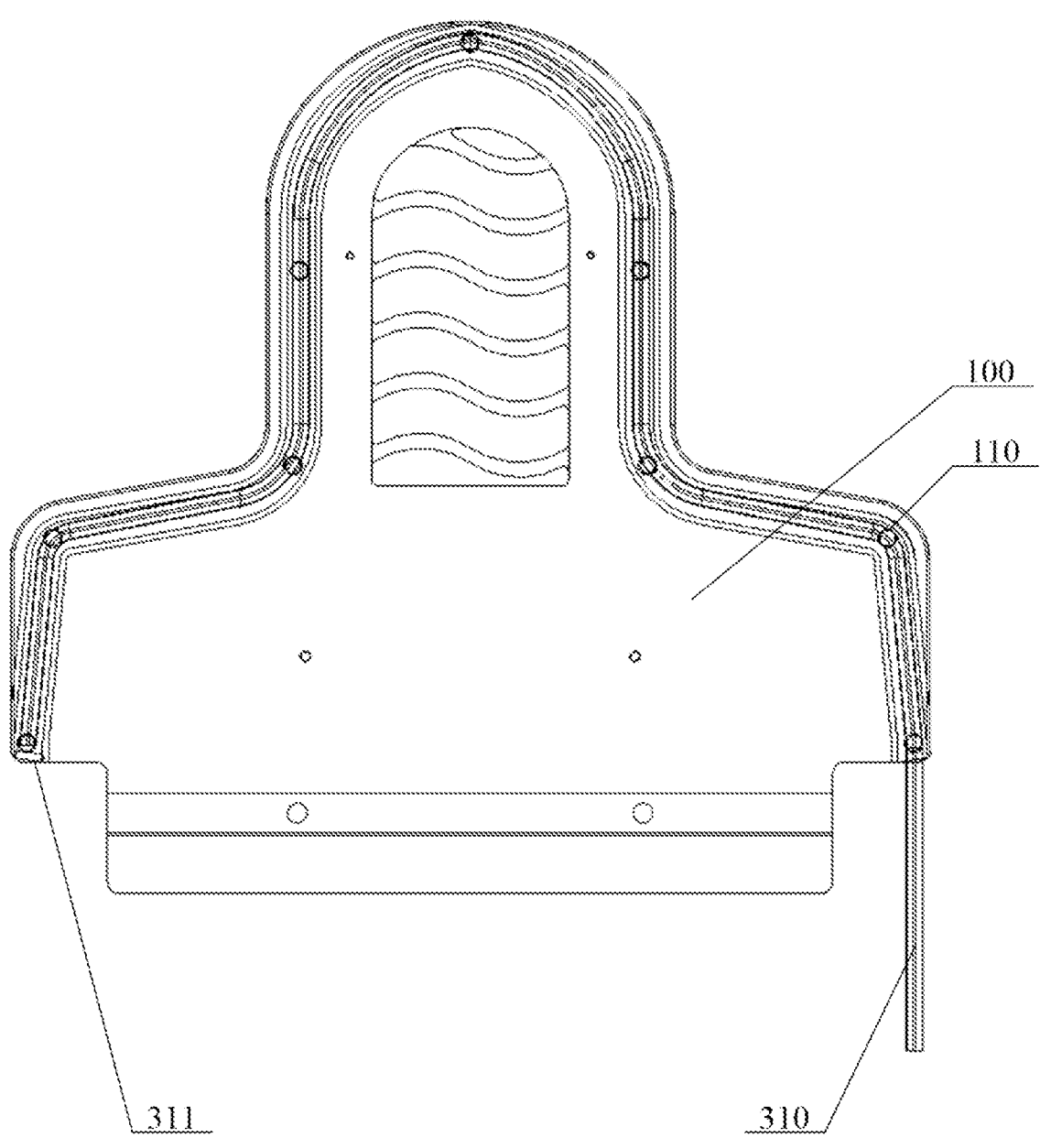
FIG. 2 is a schematic structural diagram of an unlocking assembly at a first perspective according to an embodiment of the present disclosure.
Figure 3:
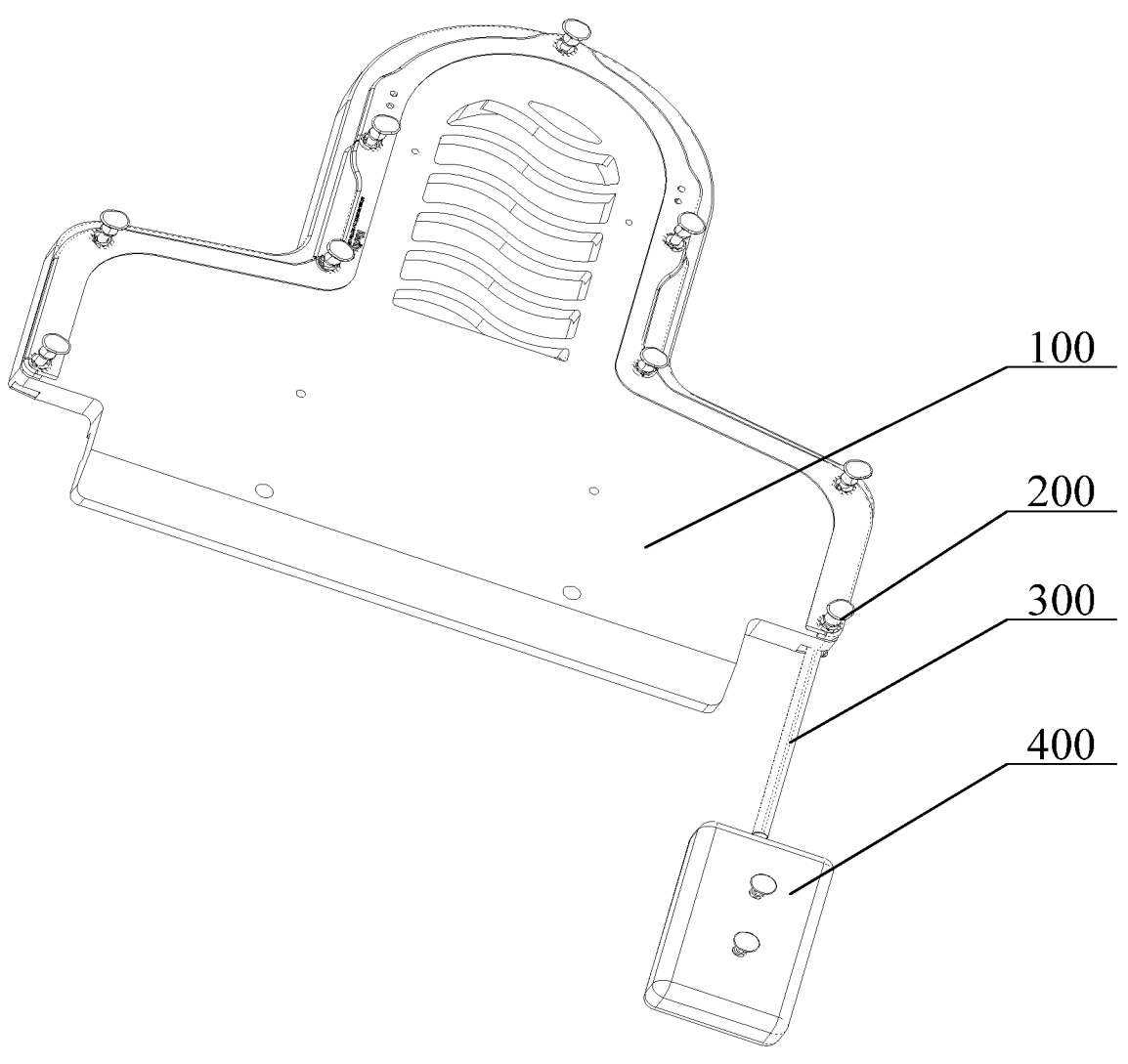
FIG. 3 is a schematic diagram of an entire structure of an unlocking assembly according to an embodiment of the present disclosure.
Figure 4:
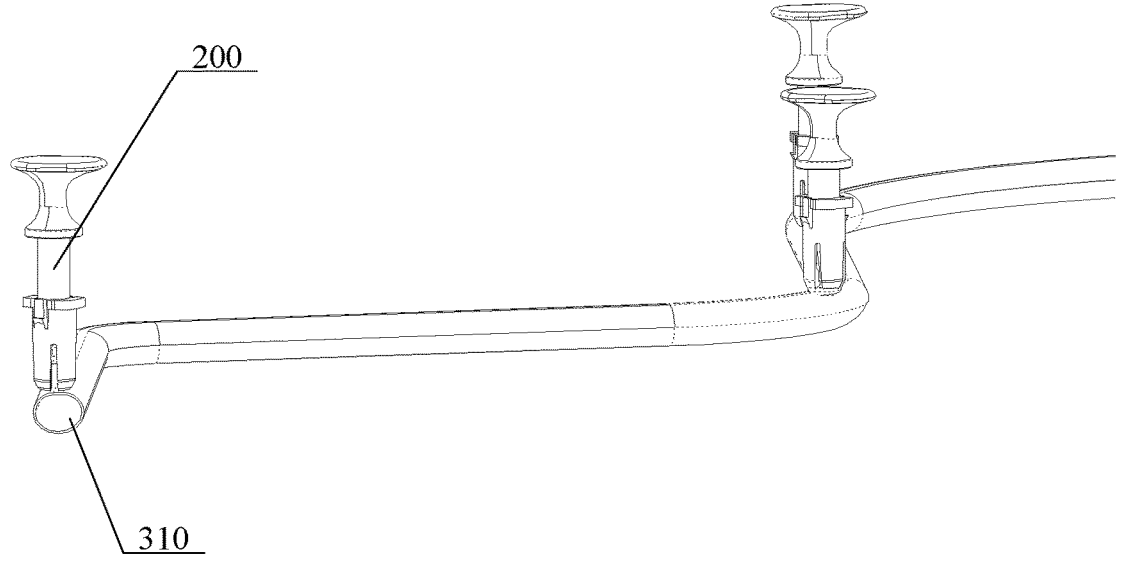
FIG. 4 is a schematic structural diagram of a locking main body and a flexible component in an unlocking assembly according to an embodiment of the present disclosure.
Figure 5:
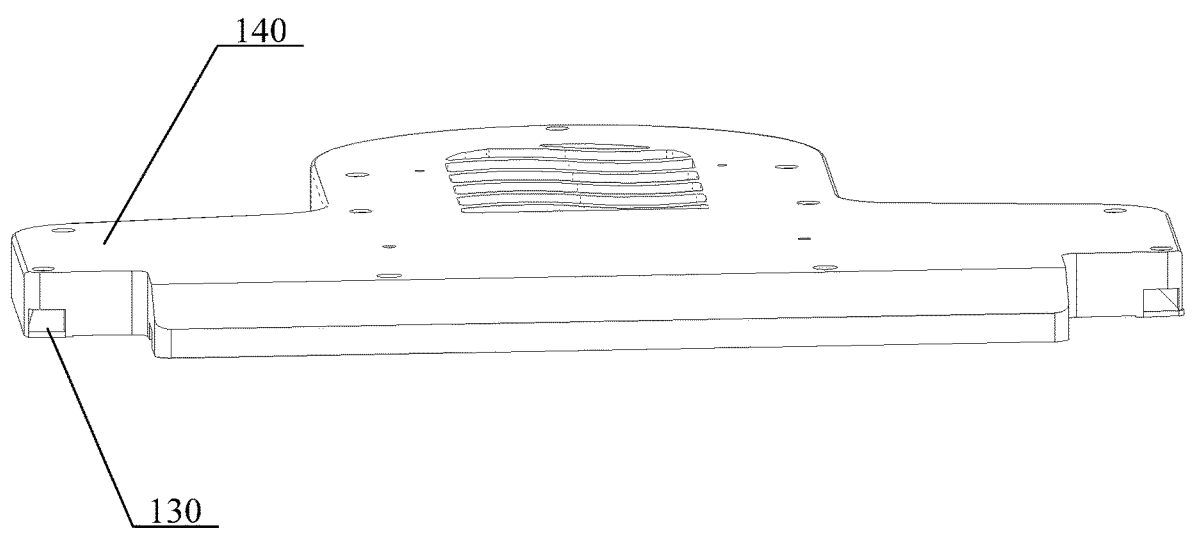
FIG. 5 is a schematic structural diagram of a fixing plate in an unlocking assembly according to an embodiment of the present disclosure.

To make the objectives, technical solutions, and advantages of embodiments of the present disclosure clearer, the technical solutions in the embodiments of the present disclosure are described below clearly and completely with reference to the accompanying drawings in the embodiments of the present disclosure. Apparently, the described embodiments are merely some rather than all of the embodiments of the present disclosure. The components of the embodiments of the present disclosure typically described and illustrated in the accompanying drawings can be arranged and designed in various configurations.

Therefore, the following detailed description about the embodiments of the present disclosure provided in the accompanying drawings is not intended to limit the scope of the present disclosure as claimed, but to represent selected embodiments of the present disclosure. All other embodiments obtained by persons of ordinary skill in the art based on the embodiments of the present disclosure without creative efforts should fall within the protection scope of the present disclosure.

It should be noted that similar numerals and letters in the following drawings represent similar items. Therefore, an item, once defined in one figure, do not need to be defined and explained in the subsequent figures.

It should be noted that in the description of the present disclosure, the orientations or positional relationships indicated by the technical terms such as "center", "top", "bottom". "left". "right", "vertical", "horizontal", "inner" and "outer" are based on the orientations or positional relationships as shown in the accompanying drawings or orientations or positional relationships for generally placing the invented product during use. These terms are merely intended to facilitate description of the present disclosure and simplify the description, rather than to indicate or imply that the mentioned apparatus or element must have a specific orientation and must be constructed and operated in a specific orientation. Therefore, these terms should not be construed as a limitation to the present disclosure. In addition, the terms "first". "second", "third", and the like are merely for distinguishing and shall not be understood as any indication or implication of relative importance.

Additionally, terms such as "horizontal," "vertical," "suspended," and the like, do not indicate an absolute requirement for components to be precisely horizontal or suspended, but they may be slightly inclined. The term "horizontal" merely indicates that the orientation is relatively more horizontal compared to "vertical," and does not imply that the structure must be completely horizontal, but that it may be slightly inclined.

In the descriptions of the present disclosure, it should be further noted that unless otherwise specified and defined explicitly, the terms "dispose", "mount", "interconnect", and "connect" should be understood in their general senses. For example, they may refer to a fixed connection, a detachable connection, or an integral connection, may refer to a mechanical connection or electrical connection, and may refer to a direct connection, an indirect connection via an intermediate medium, or an interaction between two elements. Persons of ordinary skill in the art can understand specific meanings of these terms in the present disclosure based on specific situations.

The following describes in detail some implementations of the present disclosure with reference to the accompanying drawings. In absence of conflicts, the following embodiments and features in the embodiments may be combined.

As shown in FIGS. 1 to 5, an embodiment provides an unlocking assembly, including a fixing plate 100, a locking main body 200, and a flexible component 300. The fixing plate 100 is provided with a fixing hole 110, and the locking main body 200 is movably mounted in the fixing hole 110. The flexible component 300 is connected to the locking main body 200, and the flexible component 300 is configured to be able to drive the locking main body 200 to move in a protruding direction from the fixing hole 110.

Specifically, the fixing plate 100 is provided with the fixing hole 110, with the locking main body 200 mounted in the fixing hole 110. In addition, the locking main body 200 can move up and down in the fixing hole 110, and is used to fix the low-temperature thermoplastic sheet onto the fixing plate 100, allowing for the formation of an accommodating cavity between the low-temperature thermoplastic sheet and the fixing plate 100, such that the head and neck of the human body are fixed in the accommodating cavity. When the locking main body 200 is completely inserted into the fixing hole 110 to enable a locked state, the edge of the low-temperature thermoplastic sheet is fixed by the locking main body 200, to make the low-temperature thermoplastic sheet tightly attached to the head and neck of the patient. When the locking main body 200 extends out of the fixing hole 110 to enable an unlocked state, the edge of the low-temperature thermoplastic sheet is not fixed, releasing the restraints on the head and neck of the patient.

As the flexible component 300 is connected to the locking main body 200, the flexible component 300 drives the locking main body 200 to extend along the direction of the fixing hole 110, to make the locking main body 200 in an unlocked state, such that unlocking is enabled by controlling the locking main body 200 via the flexible component 300. This replaces that unlocking is enabled only by pulling out the locking main body 200 in the prior art.

An embodiment provides an unlocking assembly, including: a fixing plate 100, a locking main body 200, and a flexible component 300. The fixing plate 100 is provided with a fixing hole 110, and the locking main body 200 is movably mounted in the fixing hole 110. The flexible component 300 is connected to the locking main body 200, and the flexible component 300 is configured to be able to drive the locking main body 200 to move in a protruding direction from the fixing hole 110. The locking main body 200 is retractably mounted in the fixing hole 110 of the fixing plate 100, and the flexible component 300 is able to drive the locking main body 200 to move in the protruding direction from the fixing hole 110, so as to release the locking between the locking main body 200 and the fixing hole 110. Therefore, the locking can be released by only controlling the flexible component 300 at a long distance, alleviating the technical problem in the related art that the fixing apparatus is unlocked only after being approached, requiring cumbersome unlocking steps and long time. In this way, during the radiation therapy, it is easy to unlock the fixing apparatus, consuming less time.

Based on the foregoing embodiment, optionally, the flexible component 300 in the unlocking assembly provided by this embodiment is disposed in the fixing plate 100 and below the locking main body 200, and the flexible component 300 is in an expanding state or a compressed state. When the flexible component 300 is in the expanding state, the locking main body 200 protrudes out of the fixing hole 110. When the flexible component 300 is in the compressed state, the locking main body 200 is inserted into the fixing hole 110.

Specifically, the fixing plate 100 is provided with a placement cavity, with the flexible component 300 in the placement cavity in the fixing plate 100. In addition, the flexible component 300 is located below the locking main body 200 and abuts against the lowest end of the locking main body 200. The flexible component 300 is in the expanding state or the compressed state. When the flexible component 300 is in the expanding state, the expansion causes a displacement in the vertical direction, generating an uplift force to lift the locking main body 200, and enabling the locking main body 200 to be in an unlocked state, thus completing unlocking. When in the compressed state, the flexible component 300 cannot lift the locking main body 200, and the locking main body 200 can be completely inserted into the fixing hole 110, completing locking.

Optionally, the unlocking assembly further includes an inflating and deflating component 400. An end of the flexible component 300 extends out of the fixing plate 100 to be connected to the inflating and deflating component 400, and the inflating and deflating component 400 is configured to be able to control the flexible component 300 to switch between an expanding state and the compressed state.

Specifically, the inflating and deflating component 400 is connected to the flexible component 300, and the inflating and deflating component 400 can deliver air into the flexible component 300, such that the flexible component 300 is controlled to be in the expanding state or the compressed state by regulating the flow of the air. When the inflating and deflating component 400 delivers air into the flexible component 300 to fill up it, the flexible component 300 is in an expanding state, thus unlocking the locking main body 200. When the inflating and deflating component 400 exhausts air from the flexible component 300, the flexible component 300 is in the compressed state, thus locking the locking main body 200.

Figure 8:
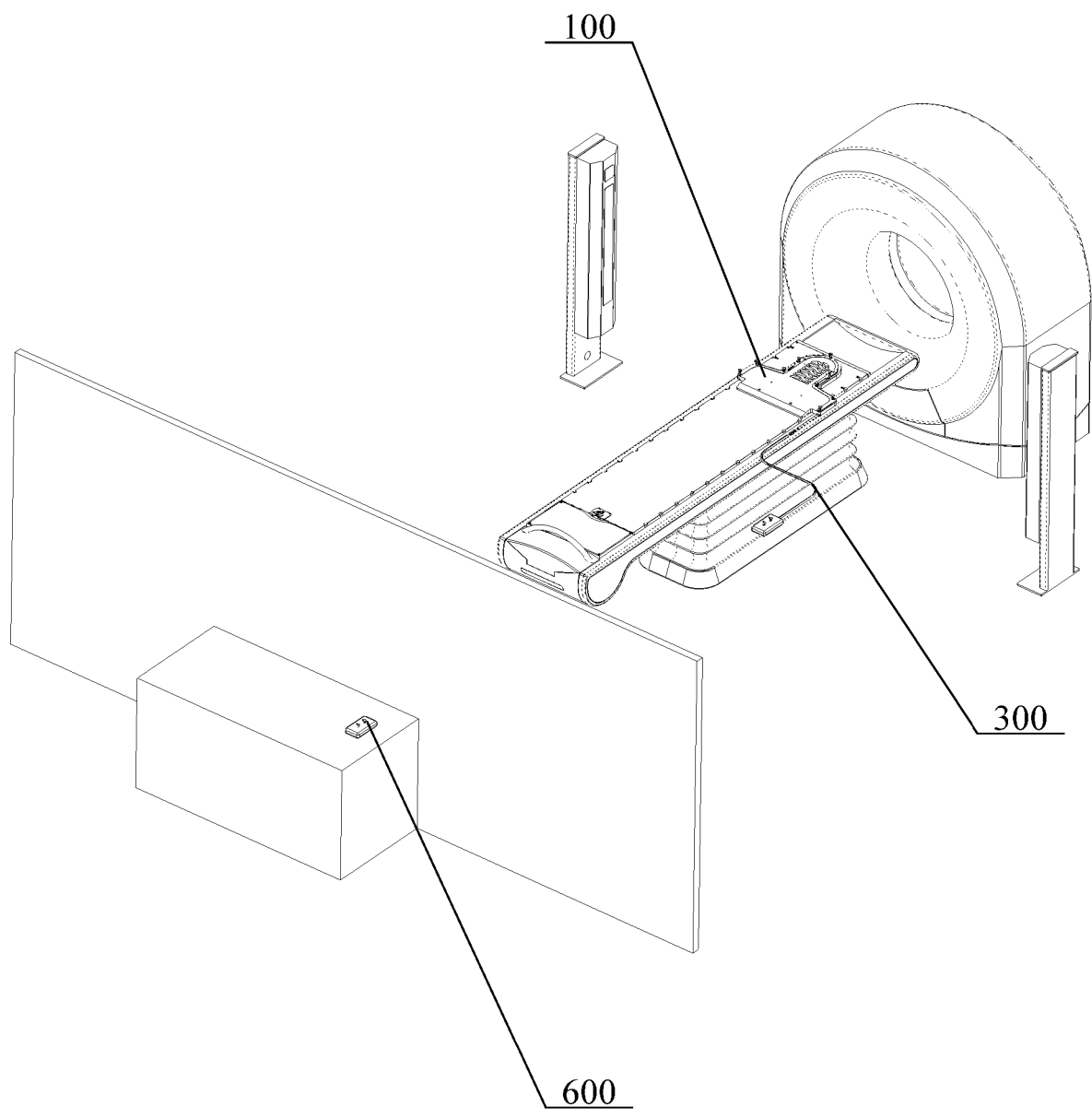
FIG. 8 is a schematic diagram of a use scenario of an unlocking assembly according to an embodiment of the present disclosure.

In addition, as shown in FIG. 8, a control apparatus 600 can be also provided. The control apparatus 600 is connected to the inflating and deflating component 400 via signal. The control apparatus 600 can generate a control signal and transmit it to the inflating and deflating component 400, so as to control the air inflation or deflation of the inflating and deflating component 400. The control apparatus 600 may be specifically arranged as a control button or a center console. The control apparatus 600 may be disposed outside the treatment room, and after detecting a special condition of the patient, the medical personnel outside the treatment room uses the control apparatus 600 to send an inflation signal to the inflating and deflating component 400, allowing the inflating and deflating component 400 to inflate the flexible component 300, thus quickly unlocking the locking main body 200.

Optionally, the flexible component 300 includes an inflatable hose 310. The fixing plate 100 is provided with a guide groove 120, the inflatable hose 310 is disposed in the guide groove 120, the locking main body 200 is provided in plurality, and the plurality of locking main bodies 200 are spaced apart along the inflatable hose 310.

Specifically, the fixing plate 100 is provided with a guide groove 120. The inflatable hose 310 extends into the guide groove 120 to be fixed in the fixing plate 100. The inflatable hose 310 is somewhat elastic. When full of air, the inflatable hose 310 is in the expanding state, generating an uplift force to lift the locking main body 200, and enabling the locking main body 200 to be in an unlocked state. When the air in the inflatable hose 310 is discharged, the inflatable hose 310 is naturally compressed, thus locking the locking main body 200.

In addition, based on special properties of a flexible material for the inflatable hose 310, a hose with a specific path is designed to match the fixing groove in size. The inflatable hose 310 is formed in the following manner: The inflatable hose 310 is made of silicone material. Based on the external profile size and cross-sectional size of the inflatable hose 310, a mold with a specific core is developed. A mixed rubber meeting a performance requirement is selected and added with additives to be compounded, and then the compound is processed to be a uniformly thick silicone extrusion material. Subsequently, the mold with a specific core is mounted at the outlet of the silicone extrusion machine, and after fed, the silicone extrusion machine extrudes a molded silicone hose. Next, the hose is placed into the drying tunnel and subjected to high-temperature vulcanization. The semi-finished hose processed in the drying tunnel is placed inside a customized oven at a high-temperature for 2 hours and subjected to a second vulcanization, stabilizing the performance of the silicone hose. After the edge trimming, component testing, and performance trials are conducted, the finished hose with a specific path is produced.

The locking main body 200 is provided in plurality, and the locking main bodies 200 are spaced apart along the inflatable hose 310, ensuring that the inflatable hose 310 can lift the plurality of locking main bodies 200.

Figure 7:
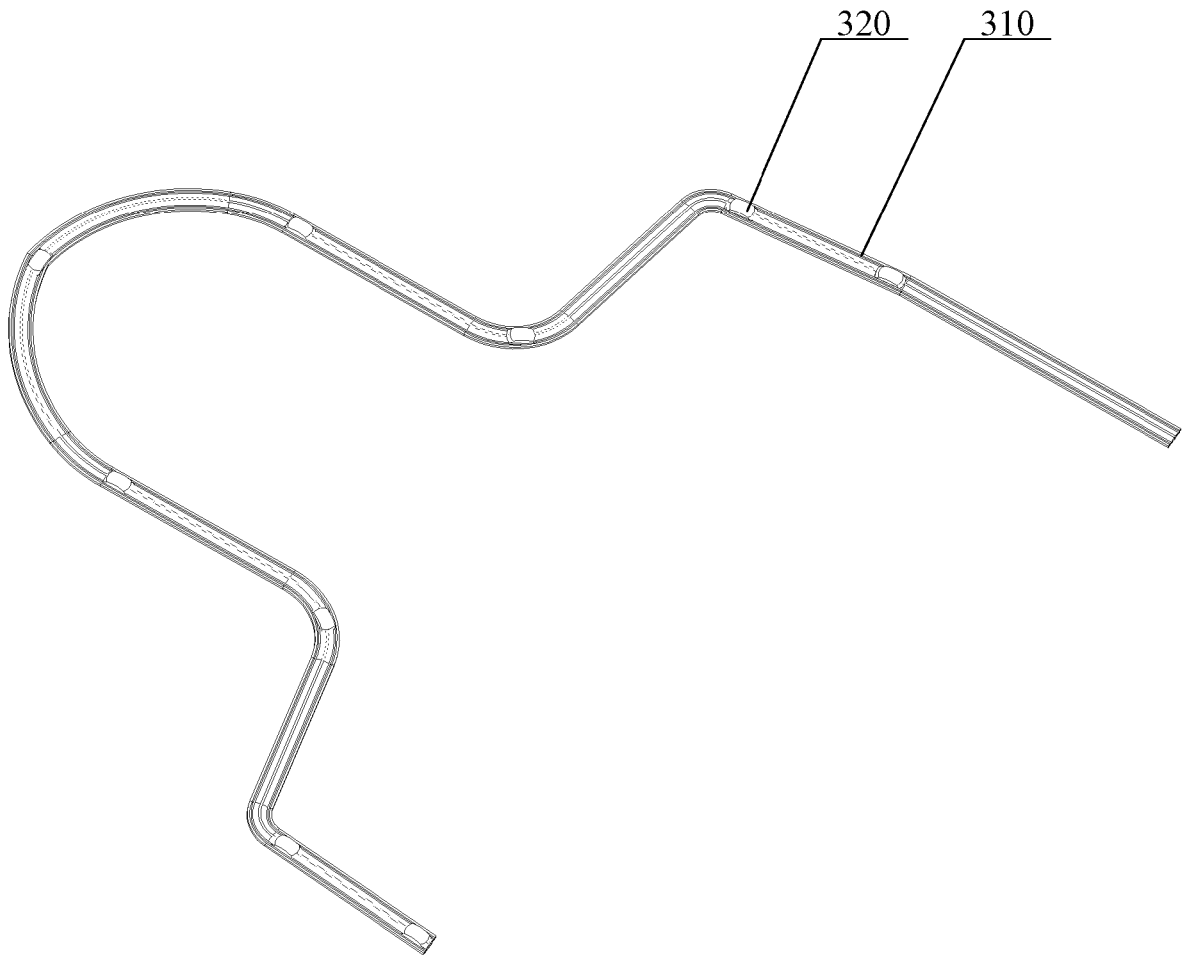
FIG. 7 is a schematic structural diagram of an inflatable hose with an air-bag protruding portion in an unlocking assembly according to an embodiment of the present disclosure.

Optionally, as shown in FIG. 7, the flexible component 300 further includes an air-bag protruding portion 320. The air-bag protruding portion 320 is disposed on the inflatable hose 310, and the air-bag protruding portion 320 abuts against the locking main body 200.

Specifically, when having a small diameter, the inflatable hose 310 may be provided with an air-bag protruding portion 320 to increase the vertical displacement range of the inflatable hose 310. The air-bag protruding portion 320 is in communication with the inflatable hose 310. When the inflatable hose 310 is inflated, the air-bag protruding portion 320 is more expandable than the inflatable hose 310, generating a vertical displacement, thus lifting the locking main bodies 200.

The air-bag protruding portion 320 is formed in the following manner: The air bag is made of a TPU material. A compression mold is designed, and the mold is coated with a special Teflon layer on both the top and bottom. Subsequently, the material is formed by hot pressing, at a heating temperature of 100° C. to 110° C. The TPU material is enabled to bulge on one side by applying pressure for a period, followed by cutting and high-frequency welding to seal it with another TPU material, so as to form an air bag with a bulge.

In the unlocking assembly provided by this embodiment, the inflating and deflating component 400 is provided to deliver air into the flexible component 300, to control the flexible component 300 to switch between the expanding state and the compressed state, thus controlling the locking and unlocking of the locking main body 200. The air-bag protruding portion 320 is disposed on the inflatable hose 310, to increase the diameter range of the inflatable hose 310. When the inflatable hose 310 is inflated, the air-bag protruding portion 320 bulges to lift the locking main body 200.

Figure 6:
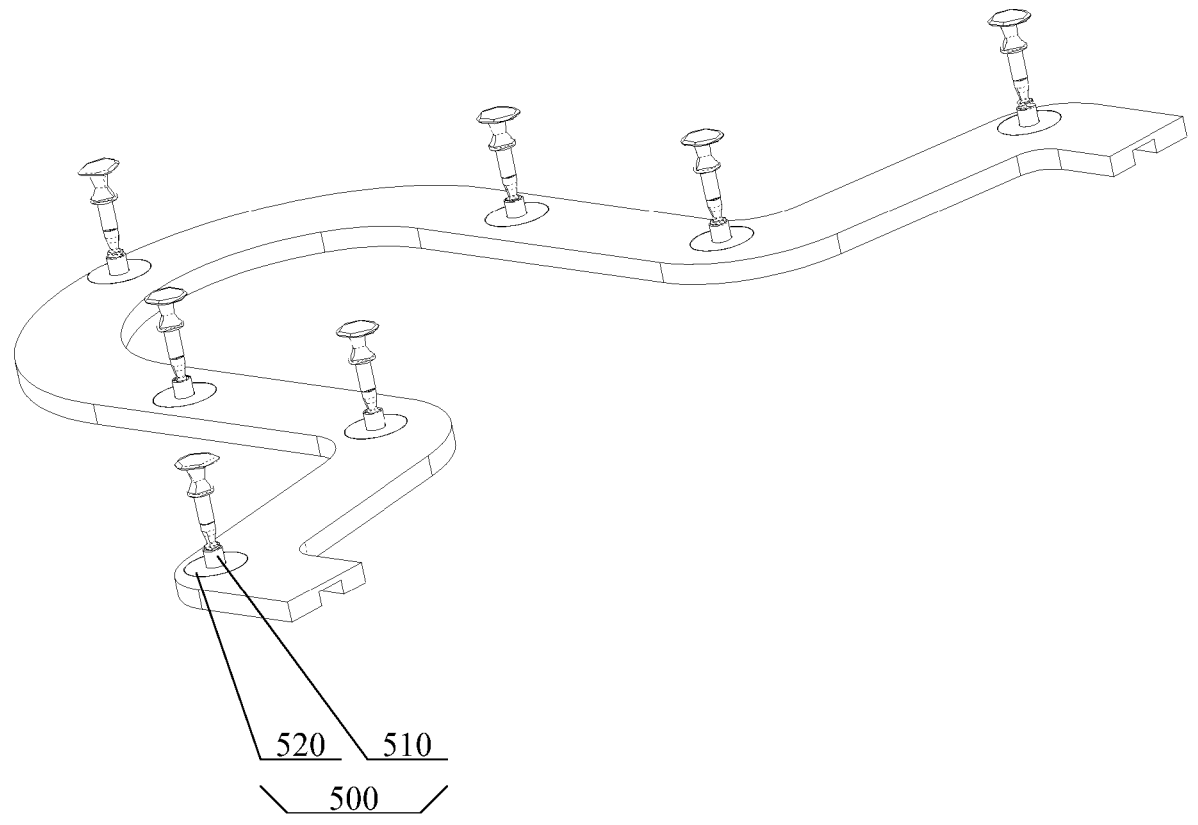
FIG. 6 is a schematic structural diagram of a locking main body with an extending portion in an unlocking assembly according to an embodiment of the present disclosure.

Based on the foregoing embodiment, as shown in FIG. 6, optionally, an end of the locking main body 200, in the unlocking assembly provided by this embodiment, close to the flexible component 300 is provided with an extending portion 500 configured to increase an overall length.

Specifically, the lower end of the locking main body 200 is provided with an extending portion 500, to increase the overall length of the locking main body 200, ensuring that the flexible component 300 can effectively lift the locking main body 200, thus quickly unlocking the locking main body 200.

Optionally, the extending portion 500 includes a stud 510 and a limit ring 520. The stud 510 is connected to the locking main body 200, the limit ring 520 is connected to an end of the stud 510 away from the locking main body 200, the limit ring 520 includes an abut surface, and the abut surface abuts against the flexible component 300.

Specifically, the stud 510 is disposed below the locking main body 200 to be connected to the locking main body 200. The limit ring 520 is disposed at the bottom of the stud 510, and includes an abut surface. During expansion of the flexible component 300, the flexible component 300 comes into contact with the abut surface of the limit ring 520, to lift the locking main body 200 via the abut surface.

Optionally, the abut surface of the limit ring 520 abuts against the air-bag protruding portion 320.

Optionally, the extending portion 500 includes an abut surface, and the abut surface abuts against the air-bag protruding portion 320 of the flexible component 300.

Optionally, an end of the inflatable hose 310 away from the inflating and deflating component 400 is provided with a sealing plug 311.

Specifically, the inflatable hose 310 has one end connected to the inflating and deflating component 400 and the other end blocking the inflatable hose 310 by using the sealing plug 311 to prevent the air in the inflatable hose 310 from being deflated at one end away from the inflating and deflating component 400.

In addition, the inflatable hose 310 may be also sealed during manufacturing, so as to replace the sealing plug 311.

Optionally, the fixing plate 100 includes a fixing bottom plate 130 and a fixing cover plate 140. The fixing cover plate 140 covers the fixing bottom plate 130, and the flexible component 300 is clamped between the fixing cover plate 140 and the fixing bottom plate 130.

Specifically, the fixing bottom plate 130 is provided with a fixing groove, with the inflatable hose 310 fixed in the fixing groove. The fixing cover plate 140 covers the fixing bottom plate 130, to clamp the inflatable hose 310 between the fixing bottom plate 130 and the fixing cover plate 140. The fixing hole 110 is disposed on the fixing cover plate 140, such that the locking main body 200 runs through the fixing hole 110 to abut against the flexible component 300.

In the unlocking assembly provided by this embodiment, the inflatable hose 310 being provided with the sealing plug 311 avoids the air in the inflatable hose 310 being deflated. With the provision of the extending portion 500, the overall length of the locking main body 200 is increased, to ensure the flexible component 300 comes into contact with the extending portion 500, lifting the locking main body 200, thus completing the unlocking.

The human body fixing apparatus provided by this embodiment includes the unlocking assembly.

The unlocking method for an unlocking assembly provided by this embodiment includes unlocking steps: 1) controlling the flexible component 300 to drive the locking main body 200 to move in a protruding direction from the fixing hole 110 of the fixing plate 100, and 2) enabling the locking main body 200 to protrude out of the fixing hole 110, to release locking of the locking main body 200.

Further, in step 1), the inflating and deflating component 400 inflates the flexible component 300, such that the flexible component 300 switches from a compressed state to an expanding state, and the flexible component 300 drives the locking main body 200 to move in a protruding direction from the fixing hole 110 of the fixing plate 100.

Optionally, in step 1), the air-bag protruding portion 320 of the flexible component 300 pushes the abut surface of the limit ring 520, such that the flexible component 300 drives the locking main body 200 to move in the protruding direction from the fixing hole 110 of the fixing plate 100, where the extending portion 500 of the locking main body 200 includes the stud 510 and the limit ring 520.

The human body fixing apparatus provided by this embodiment achieves the same effects as the unlocking assembly provided by the foregoing embodiments, and details are not described herein again.

Finally, it should be noted that the above embodiments are merely intended to explain the technical solutions of the present disclosure, rather than to limit the present disclosure. Although the present disclosure is described in detail referring to the above embodiments, persons of ordinary skill in the art should understand that they may still modify the technical solutions described in the above embodiments, or make equivalent substitutions of some or all of the technical features recorded therein, without deviating the essence of the corresponding technical solutions from the scope of the technical solutions of the embodiments of the present disclosure.

The invention claimed is:

1. An unlocking assembly, comprising a fixing plate, at least one locking main body, and a flexible component, wherein the fixing plate is provided with a fixing hole, and the locking main body is movably mounted in the fixing hole;

the flexible component is connected to the locking main body, and the flexible component is configured to drive the locking main body to move in a protruding direction from the fixing hole;

the flexible component is disposed in the fixing plate and below the locking main body, and the flexible component is in an expanding state or a compressed state;

when the flexible component is in the expanding state, the locking main body protrudes out of the fixing hole;

when the flexible component is in the compressed state, the locking main body is inserted into the fixing hole;

the locking main body is used to fix a low-temperature thermoplastic sheet onto the fixing plate to form an accommodating cavity between the low-temperature thermoplastic sheet and the fixing plate;

the unlocking assembly further comprises an inflating and deflating component;

an end of the flexible component extends out of the fixing plate to be connected to the inflating and deflating component, and the inflating and deflating component is configured to control the flexible component to switch between the expanding state and the compressed state;

the flexible component comprises an inflatable hose;

the fixing plate is provided with a guide groove, the inflatable hose is disposed in the guide groove, when the inflatable hose is in the expanding state, the locking main body is lifted up and to be in an unlocked state, when the inflatable hose is in the compressed state, the locking main body is locked;

the at least one locking main body comprises a plurality of locking main bodies, and the plurality of locking main bodies are spaced apart along the inflatable hose.

2. The unlocking assembly according to claim 1, wherein the flexible component further comprises an air-bag protruding portion; and the air-bag protruding portion is disposed on the inflatable hose, and the air-bag protruding portion abuts against the locking main body.

3. The unlocking assembly according to claim 2, wherein an end of the locking main body facing the flexible component is provided with an extending portion configured to increase an overall length.

4. The unlocking assembly according to claim 3, wherein the extending portion comprises a stud and a limit ring; and the stud is connected to the locking main body, the limit ring is connected to an end of the stud away from the locking main body, the limit ring comprises an abut surface, and the abut surface abuts against the flexible component.

5. The unlocking assembly according to claim 4, wherein the abut surface abuts against the air-bag protruding portion.

6. The unlocking assembly according to claim 3, wherein the extending portion comprises an abut surface, and the abut surface abuts against the air-bag protruding portion of the flexible component.

7. An unlocking method for the unlocking assembly according to claim 1, comprising unlocking steps: 1) controlling the flexible component to drive the locking main body to move in the protruding direction from the fixing hole of the fixing plate, and 2) enabling the locking main body to protrude out of the fixing hole, to release locking of the locking main body.

8. The unlocking method according to claim 7, wherein in the step 1), the unlocking assembly further comprises an inflating and deflating component, the inflating and deflating component inflates the flexible component, such that the flexible component switches from the compressed state to the expanding state, and the flexible component drives the locking main body to move in the protruding direction from the fixing hole of the fixing plate.

9. The unlocking method according to claim 8, wherein in the step 1), the flexible component further comprises an air-bag protruding portion, an extending portion comprises a stud and a limit ring, the air-bag protruding portion of the flexible component pushes the abut surface of the limit ring, and the flexible component drives the locking main body to move in the protruding direction from the fixing hole of the fixing plate, wherein the extending portion of the locking main body comprises the stud and the limit ring.

10. The unlocking method according to claim 7, wherein in the step 1), the flexible component further comprises an air-bag protruding portion, an extending portion comprises a stud and a limit ring, the air-bag protruding portion of the flexible component pushes an abut surface of the limit ring, and the flexible component drives the locking main body to move in the protruding direction from the fixing hole of the fixing plate.

11. The unlocking assembly according to claim 1, wherein an end of the inflatable hose away from the inflating and deflating component is provided with a sealing plug.

12. The unlocking assembly according to claim 1, wherein the fixing plate comprises a fixing bottom plate and a fixing cover plate, wherein the fixing cover plate covers the fixing bottom plate, and the flexible component is clamped between the fixing cover plate and the fixing bottom plate.

13. A human body fixing apparatus, comprising the unlocking assembly according to claim 1.

* * * * *